United States Patent [19]
Smith et al.

[11] Patent Number: 5,589,602
[45] Date of Patent: Dec. 31, 1996

[54] METHOD OF PREPARING ISOMERIZATION CATALYST

[76] Inventors: Robert S. Smith, 1018 Buoy, Houston, Tex. 77062; Steven L. McMahon, 848 Amy Lea, Sevierville, Tenn. 37862

[21] Appl. No.: 475,153

[22] Filed: Jun. 7, 1995

Related U.S. Application Data

[62] Division of Ser. No. 150,950, Nov. 12, 1993, abandoned.

[51] Int. Cl.$^6$ ............................ C07C 5/27; B01J 23/04
[52] U.S. Cl. ..................... 585/671; 585/353; 585/664; 502/344; 427/185; 427/213
[58] Field of Search ................................. 585/664, 671, 585/353; 502/344; 427/185, 213

[56] References Cited

U.S. PATENT DOCUMENTS

| | | | |
|---|---|---|---|
| 2,818,350 | 12/1957 | Kavanagh | 427/217 |
| 3,405,196 | 4/1967 | Wolff | 585/664 |
| 3,793,382 | 2/1974 | Higuchi et al. | 585/363 |
| 3,808,152 | 4/1974 | Nagase et al. | 502/346 |
| 4,621,072 | 11/1986 | Arntz et al. | 502/504 |
| 4,675,307 | 6/1987 | Taniguchi et al. | 502/306 |

OTHER PUBLICATIONS

Chemical Engineer's Handbook, Fifth Edition, Perry & Chilton, McGraw-Hill, 1973, pp. 5–54 and 20–65 to 20–751.

*Primary Examiner*—Ponnathapura Achutamurthy
*Attorney, Agent, or Firm*—Linda K. Russell

[57] ABSTRACT

This invention provides a method of preparing an isomerization catalyst by contacting an alkali metal with catalyst support particles in a fluidized bed. After the alkali metal is uniformly dispersed on the support particles, oxygen is added to the fluidizing gas to oxidize a portion of the alkali metal.

20 Claims, 1 Drawing Sheet

METHOD OF PREPARING ISOMERIZATION CATALYST

This is a divisional of application Ser. No. 08/150,950, filed Nov. 12, 1993, abandoned.

BACKGROUND OF THE INVENTION

1. Field of the Invention

The present invention relates to a method of preparing an isomerization catalyst comprising an alkali metal on a support. The isomerization catalyst so prepared is useful in isomerizing 5-vinyl-2-norbornene ("VNB") to 5-ethylidene-2-norbornene ("ENB"). ENB is used commercially in the production of elastomeric polymers and synthetic rubber.

2. Description of the Prior Art

An isomerization catalyst prepared by contacting an alkali metal with a high surface area support material such as alumina is described in U.S. Pat. No. 3,405,196. The contacting is accomplished by agitation under an atmosphere of inert gas. The agitation to disperse alkali metal on the support material described by the patent is stirring. A fluidized bed is used to treat that catalyst with oxygen. U.S. Pat. No. 3,793,382 describes dissolving an alkali metal in a solvent, for example a liquid ammonia, and spraying the solvent/alkali metal onto a carrier, for example alumina. The prior art does not describe dispersion of alkali metal onto supports utilizing a fluidized bed. The prior art methods of mechanically mixing alkali metal with supports and mixing using liquid solvents and/or slurries suffer from several disadvantages, including relatively long mixing times, uneven distribution of alkali metal on the support, breakage of the alumina particles (attrition), batches of catalyst that are relatively small and an inability to convert to a continuous process. These and other disadvantages of the prior art are overcome by the present invention.

SUMMARY OF THE INVENTION

The present invention relates to a method of preparing an isomerization catalyst by dispersing a molten alkali metal on a support within a fluidized bed environment. The fluidized bed can be established by introducing support particles to a vessel having an inlet and outlet through which an inert gas is respectively introduced and withdrawn in a manner that suspends the support particles in the inert gas. Alkali metal may be introduced to the fluidized bed and the temperature of the fluidized bed maintained above the melting point of the alkali metal so that the movement of the support particles that occurs in the fluidized bed disperses the alkali metal onto the support particles. Optimizing the operating conditions in the fluidized bed provides for more uniform and quicker dispersion of alkali metal, resulting in a superior isomerization catalyst when compared to catalysts prepared by prior art methods.

In one aspect the invention comprises a method of preparing an isomerization catalyst comprising introducing an alkali metal into a fluidized bed of support particles wherein said fluidized bed is maintained at a temperature above the melting point of the alkali metal and the support particles are maintained in a fluidized state for a time sufficient to evenly disperse the alkali metal on the support particles. In another aspect the invention comprises a method of preparing an isomerization catalyst which comprises: (a) introducing support particles into a fluidization zone, (b) introducing a flow of fluidizing gas to said fluidization zone at a rate sufficient to suspend said support particles as a dense fluidized bed maintained in said fluidization zone, (c) maintaining the temperature in the fluidization zone at a premixing temperature, (d) introducing an amount of alkali metal into said fluidization zone at a rate of 0.01 to 0.45 lb alkali metal per hour per lb of support particles, (e) maintaining said flow of fluidizing gas for a mixing period to disperse said alkali metal on said support particles to form an isomerization catalyst, and (f) withdrawing said isomerization catalyst from said fluidization zone.

Another aspect of this invention comprises isomerizing VNB to ENB using an isomerization catalyst prepared in accordance with the methods set forth herein. Contacting VNB with the isomerization catalyst under isomerization conditions will produce ENB.

A feature of this invention is that the isomerization catalyst produced in accordance with this method shows improved properties in comparison to prior art isomerization catalysts. Another feature of this invention is the improved uniformity of dispersion of the alkali metal on the support. These and other features of the invention will be apparent from the following detailed description of the invention wherein reference is made to the Figure in the accompanying drawings.

DETAILED DESCRIPTION OF THE INVENTION

Figure 1:
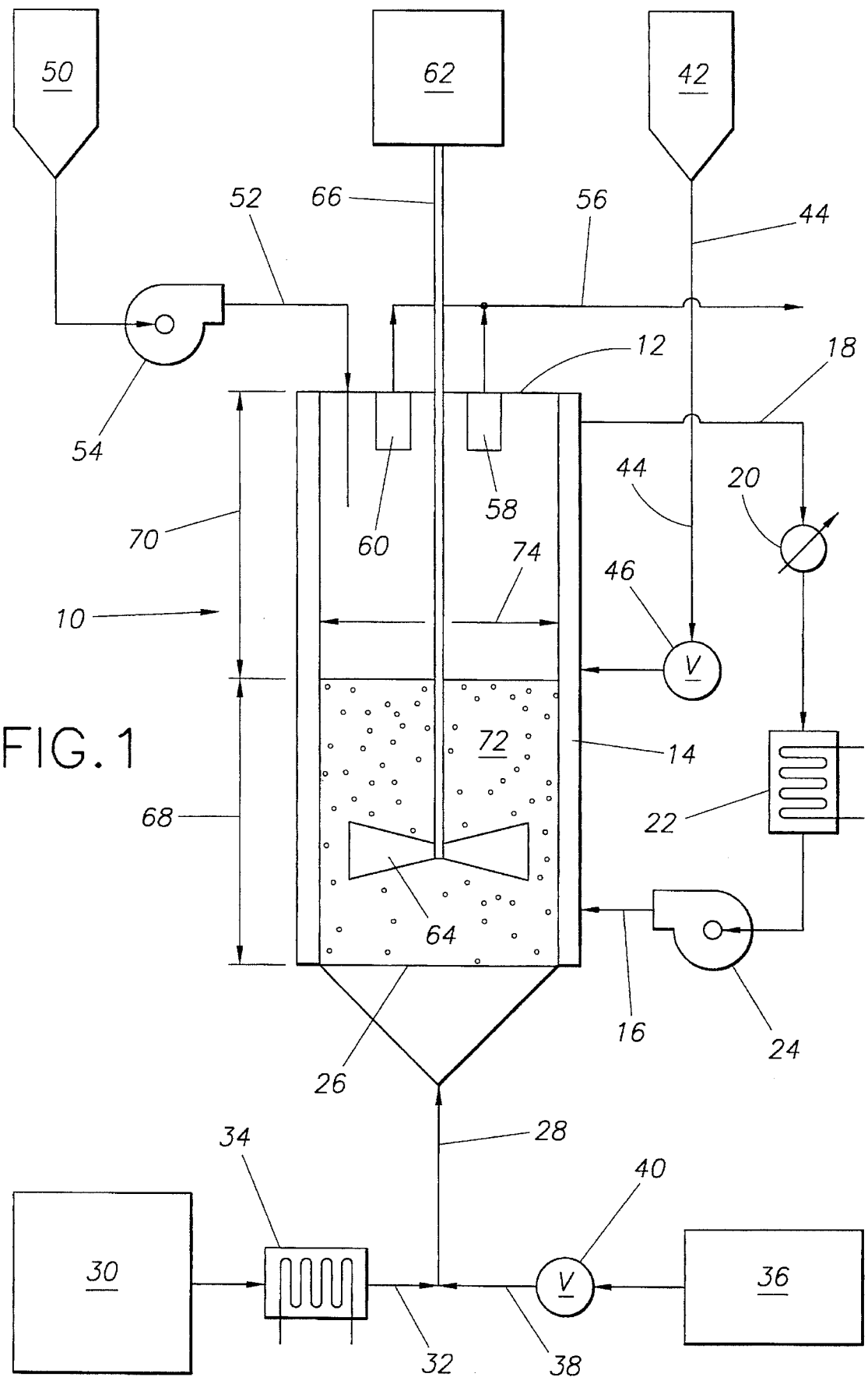
FIG. 1 is a schematic drawing of one embodiment of a fluidized bed apparatus that can be used to practice the process of preparing an isomerization catalyst in accordance with this invention.

This invention relates to an isomerization catalyst that is prepared by contacting an alkali metal with a particulate support material. In a preferred but optional embodiment, the isomerization catalyst is contacted with oxygen after the alkali metal has been dispersed upon the support particles. The support particles useful in preparing the isomerization catalyst according to this invention include alumina, silica, aluminosilicates (including zeolites and molecular sieves), hydrotalcites, carbon (including charcoal and graphite) oxides of metals of Groups 2A, 3B and 4B of the Periodic Table of Elements, clays and combinations thereof. References to the Periodic Table in this application are to CRC Handbook of Chemistry and Physics, CRC Press, Cleveland, Ohio, 53rd Edition, 1972–1973. A preferred support particle is alumina including alpha, eta, chi, theta, kappa, gamma, delta, aluminas. Gamma alumina is particularly preferred. Descriptions of alumina characteristics in this specification also apply to support particles in general.

The water content of alumina that may be used as a support material will depend partly on the type of alumina and will generally be in the range of 0 to 10% by weight (water/alumina+water). The water content of alumina referred to here is the total amount of water contained by the alumina, including adsorbed water. Optionally the alumina may be dried, as discussed further herein, to reduce the water content to a preferable range. The surface area of the alumina, measured by the B.E.T. Nitrogen Adsorption method will generally range from 5 to 300 $m^2/g$, and more preferably from 140 to 300 $m^2/g$. Presently, gamma alumina having a surface area of 140 to 180 $m^2/g$ is most preferred. Although not critical to the invention, the pore volume of the alumina, measured by the B.E.T. Nitrogen Adsorption method, is generally in the range of 0.1 to 1.0 ml/g.

Suitable alumina is available commercially from a number of suppliers. Alumina is generally available in various shapes and particle sizes. The shape of alumina particles useful in this invention is not critical, but spherical shaped particles are preferred because attrition losses are smaller. The size of the alumina particles should be selected to permit fluidization of the alumina particles in the fluidized bed apparatus. An apparatus having a capacity for a relatively strong flow of fluidizing gas will be able to fluidize larger alumina particles than an apparatus having a weaker flow of fluidizing gas. In this invention, the diameter of the alumina particles in microns should range from 10 to 500, preferably 10 to 400 and most preferably 10 to 200. Most fluidized bed systems having adjustable fluidizing gas flow rates will be capable of fluidizing alumina support particles of this size.

The alumina particles are introduced to a fluidized bed apparatus. The initial introduction of alumina may occur before fluidization gas begins to flow or, alternatively, the alumina particles may be introduced while the fluidization gas is flowing. Alumina particles may be introduced to the fluidized bed by means known to those skilled in fluidized bed technology, including without limitation conveyor belts, screw feeders, and gravity feed from a storage hopper. The process may be operated in batch, semi-continuous or continuous modes. In continuous operation, alumina will be introduced to the fluidized bed at a predetermined usually constant rate selected to provide appropriate residence time for the alumina in the fluidized bed as further described herein. At the same time, alumina particles coated with alkali metal will be withdrawn from the fluidization zone.

Parameters to be determined for successful operation of a fluidized bed are described in the literature, e.g. Chemical Engineer's Handbook, Fifth Edition, Perry & Chilton, McGraw-Hill, 1973, which is incorporated herein by reference, especially pp. 5–54 and 20–65 to 20–75, M. Leva, Fluidization, McGraw-Hill, New York, 1959, and G. F. Froment and K. B. Bischoff, *Chemical Reaction Analysis and Design*, p. 667, John-Wiley & Sons, New York, 1979. A fluidized bed may be established in a vessel having a gas inlet located below the fluidization zone and a gas outlet located above the fluidization zone. During operation of the fluidized bed apparatus, fluidization gas flows into the fluidization zone from the gas inlet upward through the fluidized bed and then out of the fluidization zone through the gas outlet. As the downward force of the earth's gravity on the alumina particles is counterbalanced by the opposing flow of fluidizing gas, the alumina particles are suspended in the fluidization zone. Preferably the fluidization zone is vertical, having a fluidizing gas inlet at the bottom and a fluidizing gas outlet at the top of the fluidization vessel.

The flow of fluidizing gas should be maintained at a rate sufficient to suspend the alumina particles in the fluidization zone and below a rate where gas slugging occurs. Gas slugging is an undesirable condition in a fluidized bed where large pockets of fluidization gas travel upward through the bed. Proper suspension of alumina particles in the fluidization zone will not occur unless the flow rate of the fluidization gas is maintained within certain ranges. Several variables will affect the flow rate that is optimum, as described in the Chemical Engineers Handbook, including without limitation the density, shape and amount of alumina particles in the fluidization zone, and the density of the fluidizing gas. The flow rate should be just above the minimum fluidization velocity and below the terminal fluidization velocity. Terminal fluidization velocity can be calculated by Stokes law or other similar methods. The object of fluidization in this invention is to achieve agitation and mixing without causing attrition of support particles. Generally, the optimum flow rate for the fluidization gas can be easily determined by testing at various fluidization gas flow rates to determine which rate provides the best fluidization under the particular circumstances. Usually the flow rate (superficial velocity) of the fluidizing gas will be maintained from 0.15 to 6.1 meters per minute (0.5 to 20 linear feet per minute), preferably 0.61 to 6.1 m/minute (2 to 20 ft/min), more preferably 1.2 to 3.7 meters per minute (4 to 12 linear feet per minute), calculated based on the apparent flow rate of fluidization gas through the fluidization zone while empty, i.e., without support particles present. This flow rate is customarily referred to as the superficial velocity of the fluidization gas. At these flow rates the fluidized bed is referred to as a dense fluidized bed.

The fluidization gas that should be used during the dispersion phase of this invention is one that is inert to reaction with an alkali metal. Inert gasses such as nitrogen, helium, neon, argon, natural gas (methane) ethane, krypton, xenon, radon and mixtures of any two or more of these are suitable. Nitrogen is preferred. During the time alkali metal is introduced to the fluidized bed and dispersed (evenly distributed) on the support particles, the entire fluidized bed should be maintained in an inert atmosphere. Utilizing a fluidizing gas consisting essentially of the inert gasses listed above will maintain an acceptably inert atmosphere.

The fluidization gas should be relatively dry since water vapor is reactive with alkali metals. Generally the fluidization gas will be sufficiently dry if the water content of the fluidization gas is below 10 ppm. If necessary, the fluidizing gas may be dried prior to contact with alkali metal. Means for drying a gas are known in the art, including passing the fluidization gas through a bed of molecular sieves, anhydrous alumina or anhydrous calcium sulfate.

Optionally, the fluidized bed may be utilized to pretreat the alumina. The pretreatment of alumina will prepare the alumina to receive the alkali metal, and adjust the water content of the alumina to appropriate levels. This pretreatment step is a type of preparation generally described in the art as calcination. The alumina pretreatment is accomplished by introducing alumina to the fluidized bed apparatus and then beginning fluidization without adding alkali metal to the alumina. Preferably the fluidizing gas is heated to promote removal of water from the alumina during pretreatment. Due to the good heat transfer between fluidizing gas and alumina that is inherent with a fluidized bed, the alumina particles will be maintained at the same temperature as the fluidizing gas. The temperature of the fluidizing gas during the pretreatment step should be maintained from 100° to 400° C., preferably 200° to 400° C., most preferably 300° to 400° C. The residence time of alumina particles in the fluidization zone during the pretreatment step should range from 0.5 to 5, preferably 1 to 4 and most preferably 1 to 2 hours. If the water content of alumina is to be reduced during the pretreatment step, the residence time may need to be adjusted to accommodate removal of the appropriate mount of water. If more water is to be removed, increasing the residence time and/or temperature of the fluidizing gas will facilitate the appropriate water removal. If relatively large amounts of water are to be removed, pretreatment may be extended beyond 4 hours. After the pretreatment step and before alkali metal is contacted with the alumina particles, the temperature of the fluidizing gas can be reduced to the appropriate temperature for contact between alumina and the alkali metal. Continued fluidization at the lower temperature will cool the alumina to a temperature that is appropriate for contact between alkali metal and alumina.

Any alkali metal or combination of alkali metals may be contacted with the alumina particles to produce the isomerization catalyst of this invention. In this application, the term alkali metal means such individual alkali metals and/or combinations of alkali metals unless the context in which the term is used expressly indicates a contrary intention. Specific alkali metals include lithium, sodium, potassium, rubidium and cesium. Sodium and potassium are preferred, and of the two, sodium is preferred. The alkali metal should be contacted with alumina particles at a temperature that is above the melting point of the particular alkali metal. For sodium the preferred contact temperature is 100° to 200° C.

Pure alkali metal may be introduced to the fluidization apparatus in either a solid or molten liquid form. Once the alkali metal is introduced, the temperature in the fluidization zone will melt any solid alkali metal introduced and maintain any molten alkali metal in the molten liquid state. Preferably, the alkali metal is introduced to the fluidization zone in a molten (liquid) state. The alkali metal is preferably introduced to the fluidization zone at a constant rate, continuously over a period of 1 to 3 hours. Preferably the temperature at which sodium is added ranges from 110° to 200° C.

The amount of alkali metal that should be added to make the isomerization catalyst of the invention is generally in the range of 5 to 20 parts based upon 100 parts of alumina by weight (a ratio in the range of 1:20 to 1:5), preferably 5 to 15 and most preferably 10 to 15 parts of alkali metal to 100 parts of alumina. In a preferred embodiment of the invention, the alkali metal is added to the fluidized bed at a certain optimum rate ranging from 0.01 to 0.45 kg/hr per kg (0.01 to 0.45 lb/hr per lb) of alumina support particles, preferably 0.05 to 0.10, while maintaining the temperature in the fluidization zone within the range of 110° to 200° C. Optionally, during the addition of alkali metal, mechanical agitation of the fluidized bed at low speeds with a turbine agitator at a tip speed of 0.003 m/s to 0.61 m/s (0.01 to 2 ft/s tip speed) may help break up larger agglomerates of alkali metal and support particles that may otherwise form in the bed.

Suspension of the alumina particles in the fluidization zone should continue during the addition of alkali metal and usually for a time thereafter. The period of time after substantially all the alkali metal has been added during which fluidization continues at a temperature above the melting point of the alkali metal is referred to herein as the mixing period, and is preferably at least 30 minutes in duration. The continued fluidization of the alumina particles during the mixing period breaks larger alkali metal/support particle agglomerates into smaller individual particles of support material coated with alkali metal and provides for uniform dispersion of the alkali metal onto the alumina particles, and may optionally be continued for 1 to 4 hours. Generally, continued fluidization of the alumina for a mixing period of 1 to 2 hours after all of the alkali metal has been introduced to the fluidization zone will provide sufficient time for the alkali metal to be evenly dispersed on the alumina particles. The degree of uniformity of the dispersion of alkali metal can be determined by measuring the conversion of alkali metal when contacted with oxygen.

Another optional feature provided by this invention is the ability to produce an oxidized alkali metal isomerization catalyst. In accordance with this feature of the invention, oxygen or an oxygen containing gas is mixed with the fluidizing gas in certain proportions. As the fluidizing gas supports the alkali metal/alumina particles, the oxygen in the fluidizing gas reacts with the alkali metal in an exothermic reaction that liberates 50 kcal of heat per g-atom of alkali metal reacted. Oxygen or oxygen containing gas is introduced to the fluidized bed at a relatively constant rate that is determined by heat transfer characteristics of the fluidized bed system. The temperature of the particles in the fluidized bed during oxidation is maintained below 250° C., and preferably below 200° C. The total amount of oxygen ($O_2$) added should range from 0.001 to 0.2 moles based upon each mole of alkali metal dispersed on the support particles. The oxygen is preferably added to the fluidizing gas prior to the gas distributor in the fluidizing apparatus. The temperature of the fluidized bed is preferably maintained from 150° to 200° C. The optimum molar oxidation level is from 0.15 to 0.20:1 ($O_2$:Alkali metal). The rate at which oxygen is introduced to the fluidization zone is preferably in the range from 0.01 to 2 moles $O_2$ per hour per mole of alkali metal, more preferably 0.01 to 0.2 and most preferably 0.01 to 0.1 moles/hr per mole of alkali metal on the support particles.

Optionally, a helical, paddle type or turbine agitator may be used to provide supplemental agitation to the alumina particles. The fluidized bed apparatus is constructed so the agitator is deployed in the fluidized bed portion of the support particles. The agitation velocity should be low to avoid attrition.

The invention may be further understood by reference to FIG. 1 which shows a fluidizing apparatus 10. The fluidizing apparatus 10 comprises a vessel 12, an alkali metal reservoir 50, a support particle reservoir 42 and a gas supply 30. Support particles may be charged to vessel 12 from support particle reservoir 42 through feed conduit 44 which connects support particle reservoir 42 with vessel 12. The flow of support particles into vessel 12 may be controlled or restricted by control valve 46. Control valve 46 may be a slide valve, star valve, table feeder, screw feeder, cone valve or any other similar device used to control flow of solid particles.

Support particles may be charged to vessel 12 either continuously during fluidization or support particles may be charged as a batch all at once to vessel 12 prior to or during fluidization. After support particles have been charged to vessel 12, they may be fluidized with a fluidizing gas. In FIG. 1, gas supply 30 provides the fluidizing gas to gas inlet 28 which is in communication with the bottom of vessel 12. Gas inlet 28 is connected with gas supply conduit 32 through which fluidizing gas flows from gas supply 30. If necessary, the fluidizing gas may be heated by passing it through gas pre-heater 34.

Fluidizing gas enters vessel 12 through gas inlet 28 and then passes through gas distributor plate 26 which is positioned near the bottom of vessel 12. Support particles are maintained in fluidized bed 72 in the space above gas distributor plate 26. Fluidizing gas travels up through gas distributor plate 26 through fluidized bed 72 and out of vessel 12 through gas outlet 56. Gas outlet 56 is connected to the upper portion of vessel 12 to avoid removing support particles that are entrained in the flow of fluidizing gas through vessel 12. Optionally, filters 58 and 60 allow for passage of the fluidizing gas therethrough but filter out entrained support particles so that they stay within vessel 12. The fluidizing gas may be discharged from the system or recycled back to gas supply 30.

The fluidized bed depth is the distance between gas distribution plate 26 and the top of fluidized bed 72 and is represented in FIG. 1 by line 68. Preferably, vessel 12 provides for disengaging space above the fluidized bed 72. The disengaging space is the volume above the top of fluidized bed 72 and below the top of vessel 12, and the disengaging space depth is represented by reference character 70. The disengaging space provides for separation of support particles (which fall back down into fluidized bed 72) from the flowing fluidized gas which is withdrawn through gas outlet 56.

Alkali metal is added to fluidized bed 72 from alkali metal reservoir 50 through feed conduit 52. Feed pump 54 may be used to meter the proper amounts of alkali metal into vessel 12.

Optionally, vessel 12 may be equipped with a turbin agitator 64 connected to motor 62 by shaft 66. In operation, turbin agitator 64 rotates to provide an agitation in the fluidized bed in addition to that provided by fluidization.

After all of the alkali metal that is to be added to the support particles has been added, and the alkali metal has been uniformly distributed upon the support particles, oxygen may be added to vessel 12 to react with the alkali metal. Oxygen from oxygen supply 36 is introduced to vessel 12 through supply conduit 38 which is connected m gas inlet 28. The flow of oxygen through supply conduit 38 may be controlled by control valve 40. Addition of oxygen should be controlled at a rate so that the temperature of fluidized bed 72 does not exceed temperature limits as described in this specification.

In order to provide for better temperature control of vessel 12, it may be necessary to install a heat exchanger 14 around vessel 12. In FIG. 1, heat exchanger 14 is an oil jacket having an oil inlet 16 and an oil outlet 18. In operation, oil circulates through heat exchanger 14 to add or remove heat from fluidized bed 72 as needed. Circulation of the oil may be provided by means of oil pump 24. The temperature of the oil may be adjusted using alternatively oil cooler 20 or oil heater 22 as needed. During the pretreatment step and also during the mixing period, oil heater 22 may be used to maintain fluidized bed 72 at the desired temperature. Alternatively or in conjunction therewith, gas preheater 34 may be used. During the addition of alkali metal, it may be necessary to use oil heater 22 to keep the system at temperatures to maintain the alkali metal in a molten form. During oxygen addition, because of the exothermic oxidation reaction, it may be necessary to use oil cooler 20 to maintain the temperature of fluidized bed 72 within appropriate limits.

As discussed in the specification, the superficial velocity of the fluidizing gas is calculated with reference to vessel 12 in an empty condition. If vessel 12 is circular in cross section, the fluidizing gas flow superficial velocity may be calculated by determining the cross sectional area from diameter 74, measuring the fluidization gas flow rate and pressure and calculating the gas flux across the cross section of vessel 12.

The invention may be more fully understood by reference to the following examples.

EXAMPLE 1

This example describes a catalyst preparation where sodium metal and alumina are mixed with a stir paddle at 250 rpm in a 300 cc reactor. The tip speed of the paddle was 0.79 m/s (2.6 Pt/s). First, gamma-alumina (30 g), with a surface area of 150 $m^2/g$ is dried in a nitrogen flow at 400° C. for 1 hour and then cooled to room temperature under nitrogen. Then, small pieces of metallic sodium (4.5 g) and the alumina are placed in the nitrogen blanketed reactor and heated under nitrogen to 150° C. At the point when metallic sodium starts to melt, stirring is started and continued throughout the preparation. The mixture is stirred for 30 minutes at 150° C. and then the temperature is raised to 300° C. where stirring is continued for 60 minutes. Then the mixture is cooled to room temperature and a mixture of 5% $O_2$ in $N_2$ is added at 126 mL/minutes for 123 minutes. Total stirring time was 213 minutes. Measurement of particle size showed 25 wt % of the finished catalyst had a diameter less than 10 microns. The starting alumina had 7 wt % of particles with less than 10 micron diameter.

Particles with diameters less than 10 microns in diameter cause problems when the catalyst is used in a liquid slurry isomerization processes because the rate at which these particles will settle is too slow for efficient catalyst/liquid-product separation.

EXAMPLE 2

This example shows catalyst preparation in a commercial double cone rotating mixer. Gamma-alumina powder (11.3 kg) (25 lb) having a surface area of 170 $m^2/g$ was dried at 400° C. in a flow of nitrogen. The powder is then heated to 150° C. under a $N_2$ blanket and molten sodium (1.7 kg) (3.75 lb) is added over a period of 30–60 minutes while rotating the equipment to provide agitation. Mixing and heating at 150° C. are continued for 120 minutes. Next, a mixture of 5% $O_2$ in $N_2$ is added over a period of 120–240 minutes while maintaining mixing action and temperature between 150°–200° C. The total agitation time is between 270 and 420 minutes. Catalyst prepared in this manner was found to have 2 wt % of particles with diameters greater than 600 microns compared to the starting alumina which had none. There was no change in the amount of particles with diameters less than 10 microns. Particles with diameters greater than 600 microns cause processing problems because they tend to plug transfer lines that handle catalyst or liquid slurries in commercial isomerization plants.

EXAMPLE 3

This example shows catalyst preparation in a fluidized bed reactor with auxiliary mechanical mixing. Gamma-alumina powder (36.3 kg) (80 lb) with a surface area of 170 $m^2/g$ was added to the reactor and then fluidized with $N_2$ at a linear superficial velocity of 9 ft/min and stirred with a helical turbine at a tip speed of (0.23 m/s) (0.75 ft/s). The fluidization and stirring was maintained throughout the remainder of the preparation. The alumina was heated to 350° C. for 60 minutes, and then cooled to 150° C. over a period of 120 minutes. Then, molten sodium (5.4 kg) (12 lb) was added at a constant rate over 120 minutes at 150° C. Next, 0.954 $m^3$ (33.7 $ft^3$) of oxygen was added over a 370 minute period while maintaining the temperature between 150° and 200° C. Total mixing time was 670 minutes. Compared to the starting alumina, there was no increase in amounts of particles with diameters greater than 600 microns or less than 10 microns.

EXAMPLE 4

This example describes a catalyst preparation similar to example 1 except the alumina and reaction temperatures were chosen to match those in example 3. Sodium metal and alumina are mixed with a stir paddle at 250 rpm in a 300 cc reactor. The tip speed of the paddle was 0.79 m/s (2.6 ft/s). First, gamma-alumina (21.8 g), with a surface area of 170 $m^2/g$ is dried in a nitrogen flow at 400° C. for 1 hour and then cooled to room temperature under nitrogen. Then, small pieces of metallic sodium (3.3 g) and the alumina are placed in the nitrogen blanketed reactor and heated under nitrogen to 150° C. At the point when metallic sodium starts to melt, stirring is started and continued throughout the preparation. The mixture is stirred for 150 minutes at 150° C. Then, a mixture of 5% $O_2$ is added at 126 mL/min for 82 minutes at 150° C.

EXAMPLE 5

The degree of sodium dispersion on a catalyst can be determined by the extent to which the metallic sodium on the catalyst can be oxidized. The catalysts in examples 3 and 4 were subjected to exhaustive oxidation by adding 5% $O_2$ in $N_2$ so that the theoretical stoichiometric ratio for $Na_2O$ of 0.25/1 (moles $O_2$: moles Na) was achieved. The amounts of metallic sodium remaining on the catalysts after exhaustive oxidation were determined by $H_2$ evolution after hydrolysis. Catalyst from example 3 contained 0.9 wt % metallic sodium and catalyst from example 4 contained 4.6 wt % metallic sodium. The use of gas fluidization as a mixing technique gives a higher degree of sodium dispersability.

EXAMPLE 6

The catalysts in examples 3 and 4 were measured for activity to isomerize 5-vinyl-2-norbornene (VNB) to 5-ethylidene-2-norbornene (ENB) using VNB that contained various impurities that might be expected in commercial practice. The impurities (and their level in the VNB) were vinylacetylenecyclopentadiene adducts (720 ppm), tetrahydroindene (570 ppm), cyclooctadiene (300 ppm), and alkylvinylcyclohexenes (600 ppm). The vinylacetylenecyclopentadiene adducts are known to be catalyst poisons. The isomerizations were run by stirring 25 g of VNB with 0.35 g catalyst for 2 hours at ambient temperature. Products were analyzed by gas chromatography. The VNB conversions were 98.5% for the example 3 catalyst and 24% for the example 4 catalyst. The gas fluidization technique for mixing gives a catalyst with greater activity.

EXAMPLE 7

The catalysts in examples 2 and 3 were measured for activity to isomerize VNB to ENB using VNB that contained 1250 ppm indene as a poisoning agent. The isomerizations were run by stirring 25 g of VNB with 0.35 g catalyst for 2 hours at ambient temperature. Products were analyzed by gas chromatography. The VNB conversions were 98% for the example 3 catalyst and 30% for the example 2 catalyst. This again shows the gas fluidization technique for mixing gives a catalyst with greater activity.

We claim:

1. A method of isomerizing 5-vinyl-2-norbornene (VNB) to 5-ethylidene-2-norbornene comprising contacting VNB with an isomerization catalyst at a temperature of 0° to 80° C. and a contact time in the range of 1 to 12 hours wherein said isomerization catalyst is prepared by:

(a) introducing alumina particles having a particle diameter in the range of 10 to 500 microns into a vertical fluidization zone, (b) introducing an upward flow of fluidizing nitrogen gas to said fluidization zone at a rate sufficient to suspend said alumina in a fluidized bed maintained in said fluidization zone, (c) maintaining the temperature in the fluidization zone at a premixing temperature in the range of 150° to 400° C. to dry said alumina, and thereafter, (d) introducing an amount of sodium, wherein said amount of sodium is within the range of 1:20 to 1:5 based upon the weight of alumina particles, into said fluidization zone at a rate of 0.01 to 0.45 lb sodium/hr per lb alumina while maintaining the temperature in the fluidization zone within the range of 100° to 200° C., (e) maintaining said flow of fluidizing gas for a mixing period of at least 30 minutes after said amount of sodium has been introduced to said fluidization zone to disperse said sodium on said alumina to form an isomerization catalyst, and thereafter, (f) introducing an amount of oxygen to said fluidization zone at a rate in the range of 0.01 to 1 moles/hr per mole of sodium wherein said amount of oxygen is within the range of 0.001:1 to 0.2:1 based on the moles of oxygen introduced to said fluidization zone to the moles of said amount of sodium to form an isomerization catalyst, and (g) withdrawing said isomerization catalyst from said fluidization zone.

2. The method of isomerizing an olefin which comprises contacting a stream comprising the olefin with an activated catalyst, wherein the activated catalyst is prepared by a method comprising introducing an amount of alkali metal into a fluidized bed of support particles wherein said fluidized bed of support particles is maintained at a temperature above the melting point of the alkali metal and in a fluidized bed state for a time sufficient to evenly disperse the alkali metal on the support particles without substantial breakdown of the support particles, wherein said fluidized bed of support particles is maintained in a fluidized state utilizing a fluidizing gas flowing at a superficial velocity of from 2 to 20 linear feet per minute, and wherein the diameter of the support particles is in the range from 10 to 500 microns.

3. A method in accordance with claim 2 wherein the weight ratio of the amount of alkali metal introduced to the fluidized bed of support particles in relation to the weight of support particles in the fluidized bed is within the range of 1:20 to 1:5.

4. A method in accordance with claim 2 wherein the fluidized bed of support particles is maintained in a fluidized state utilizing a fluidizing gas selected from the group consisting of helium, neon, argon, krypton, xenon, radon, nitrogen, methane, ethane and mixtures thereof.

5. A method in accordance with claim 2 wherein the alkali metal is selected from the group consisting of lithium, sodium, potassium, rubidium and cesium.

6. A method in accordance with claim 2 wherein the fluidized bed of support particles is mechanically mixed with an agitator.

7. A method in accordance with claim 2 wherein after the alkali metal is evenly dispersed on the support particles, oxygen is introduced to the fluidized bed.

8. A method in accordance with claim 2 wherein the mole ratio of oxygen introduced to the fluidized bed in relation to alkali metal dispersed on the support particles is in the range from 0.001:1 to 0.2:1.

9. A method in accordance with claim 2 wherein the weight ratio of the amount of alkali metal introduced to the fluidized bed of support particles in relation to the weight of support particles in the fluidized bed is within the range of 1:20 to 1:5, the fluidized bed of support particles is maintained in a fluidized state utilizing a fluidizing gas flowing at a rate of from 4 to 12 linear feet per minute and selected from the group consisting of helium, neon, argon, krypton, xenon, radon, nitrogen, methane and ethane, the alkali metal is selected from the group consisting of lithium, sodium, potassium, rubidium and cesium, and wherein after the alkali metal is evenly dispersed on the support particles, oxygen is introduced to the fluidized bed in a mole ratio of oxygen to alkali metal dispersed on support particles that is in the range from 0.001:1 to 0.2:1.

10. A method in accordance with claim 9 in the support particles consist essentially of alumina and the diameter of the support particles is in the range from 10 to 500 microns.

11. The method of isomerizing a stream comprising an olefin which comprises contacting the stream comprising the olefin with an activated catalyst, wherein the activated catalyst is prepared by a method which comprises:

(a) introducing alumina particles having a particle diameter in the range of 10 to 500 microns into a vertical fluidization zone, (b) introducing an upward flow of fluidizing gas to said fluidization zone at a rate sufficient to suspend said alumina in a fluidized bed maintained in said fluidization zone, (c) maintaining the temperature in the fluidization zone at a premixing temperature within the range of 100° to 400° C., (d) introducing an amount of alkali metal selected from the group consisting of sodium, potassium, rubidium and cesium into said fluidization zone at a rate of 0.01 to 0.45 lb alkali metal/hr per lb alumina while maintaining the temperature in the fluidization zone within the range of 100° to 200° C., (e) maintaining said flow of fluidizing gas for a mixing period of at least 30 minutes after said amount of alkali metal has been introduced to said fluidization zone to disperse said alkali metal on said alumina to form an isomerization catalyst, and (f) withdrawing said isomerization catalyst from said fluidization zone.

12. A method in accordance with claim 10 wherein said amount of alkali metal is within the range of 1:20 to 1:5 based upon the total weight of alkali metal to the weight of said alumina introduced to said fluidization zone.

13. A method in accordance with claim 12 wherein the fluidizing gas is selected from the group consisting of helium, neon, argon, krypton, xenon, radon, nitrogen, methane and ethane.

14. A method in accordance with claim 13 wherein said now of fluidizing gas is maintained at a superficial velocity within the range of 4 to 12 linear feet per minute.

15. A method in accordance with claim 14 wherein said mixing period is from 1 to 3 hours.

16. A method in accordance with claim 15 which further comprises maintaining said flow of fluidizing gas after said mixing period and introducing an amount of oxygen to said fluidization zone before said isomerization catalyst is withdrawn from said fluidization zone.

17. A method in accordance with claim 16 wherein said amount of oxygen is within the range of 0.001:1 to 0.2:1 based on the moles of oxygen introduced to said fluidization zone to the moles of said amount of alkali metal.

18. A method in accordance with claim 17 wherein the rate at which said amount of oxygen is introduced to said fluidized bed is in the range of 0.01 to 0.1 moles/hr per mole of alkali metal.

19. A method in accordance with claim 18 which further comprises drying said alumina in said fluidization zone by maintaining said premixing temperature within the range of 100° to 400° C. for at least 1 hour.

20. A method in accordance with claim 19 wherein said alkali metal is sodium and said fluidizing gas is nitrogen.

* * * * *